United States Patent
Chamberlain et al.

(10) Patent No.: US 7,422,365 B2
(45) Date of Patent: Sep. 9, 2008

(54) THERMAL IMAGING SYSTEM AND METHOD

(75) Inventors: Gary Roy Chamberlain, Sheffield (GB); Andrew Mellor, Ravenfield (GB); Ian Hamilton Ridley, Sheffield (GB)

(73) Assignee: Land Instruments International Limited (GB)

( * ) Notice: Subject to any disclaimer, the term of this patent is extended or adjusted under 35 U.S.C. 154(b) by 54 days.

(21) Appl. No.: 10/554,140

(22) PCT Filed: Apr. 23, 2004

(86) PCT No.: PCT/GB2004/001778

§ 371 (c)(1), (2), (4) Date: Oct. 20, 2005

(87) PCT Pub. No.: WO2004/097389

PCT Pub. Date: Nov. 11, 2004

(65) Prior Publication Data

US 2006/0232675 A1  Oct. 19, 2006

(30) Foreign Application Priority Data

Apr. 25, 2003 (GB) .................................. 0309479.4
May 6, 2003 (GB) .................................. 0310334.8

(51) Int. Cl.
*G01J 5/02* (2006.01)

(52) U.S. Cl. ..................... 374/120; 374/129; 374/2; 374/5; 374/121; 250/341.6; 250/338.1

(58) Field of Classification Search .............. 374/1–2, 374/120, 121, 124, 129, 4.5; 702/99; 250/252.1, 250/338.1, 339.02, 339.03, 339.04, 339.09, 250/339.11, 341.5, 393, 341.1, 341.2, 341.3, 250/341.4, 341.6, 341.7, 341.8, 252.2, 493.1, 250/494.1, 495.1, 559.4, 559.41, 559.42, 250/559.43, 559.44, 559.45, 559.46, 342
See application file for complete search history.

(56) References Cited

U.S. PATENT DOCUMENTS

| | | | | |
|---|---|---|---|---|
| 1,014,769 A | * | 1/1912 | Barnes | 54/73 |
| 4,428,382 A | * | 1/1984 | Walsall et al. | 600/549 |
| 4,466,748 A | * | 8/1984 | Needham | 374/129 |
| 4,502,793 A | * | 3/1985 | Smith et al. | 374/124 |
| 4,634,294 A | * | 1/1987 | Christol et al. | 374/170 |
| 4,647,774 A | * | 3/1987 | Brisk et al. | 250/338.1 |
| 4,647,775 A | * | 3/1987 | Stein | 250/338.1 |
| 4,831,258 A | * | 5/1989 | Paulk et al. | 250/349 |
| 4,944,589 A | * | 7/1990 | Nordqvist | 356/326 |
| 5,094,544 A | * | 3/1992 | Ignatowicz | 374/126 |

(Continued)

FOREIGN PATENT DOCUMENTS

| | | | |
|---|---|---|---|
| EP | 1526377 A1 | * | 4/2005 |
| GB | 1014769 | | 12/1965 |
| JP | 05340817 A | * | 12/1993 |
| WO | WO 03/077539 A1 | | 9/2003 |

OTHER PUBLICATIONS

Brown, T. J., "Image processing hardware and software for the 90-element pushbroom infared/charge-coupled device/multiplexer (IR/CDD/MUX) field test instrument," *Proc. Soc. Photo-Optical Instrumentation Engineers*, 253:86-106 (1980).

(Continued)

*Primary Examiner*—Gail Verbitsky
(74) *Attorney, Agent, or Firm*—Townsend and Townsend and Crew LLP

(57) ABSTRACT

A thermal imaging system and method for quantitative thermal mapping of a scene. The system comprises a thermal imaging device, a heat source of known temperature and emissivity located within the scene viewed by the thermal imaging device and a processor adapted to generate a calibrated temperature map of the scene from the data supplied by the thermal imaging device, based on the known temperature of the heat source. This enables accurate temperature measurements to be made using inexpensive uncooled Focal Plane Array detectors.

59 Claims, 3 Drawing Sheets

U.S. PATENT DOCUMENTS

| | | | | |
|---|---|---|---|---|
| 5,128,884 | A | * | 7/1992 | Prager .................... 702/99 |
| 5,265,958 | A | * | 11/1993 | Ludlow .................... 374/2 |
| 5,272,340 | A | | 12/1993 | Anbar |
| 5,420,419 | A | * | 5/1995 | Wood .................... 250/338.4 |
| 5,675,149 | A | * | 10/1997 | Wood et al. ............. 250/332 |
| 5,746,511 | A | * | 5/1998 | Eryurek et al. ............ 374/2 |
| 5,775,806 | A | * | 7/1998 | Allred .................... 374/124 |
| 5,850,623 | A | * | 12/1998 | Carman et al. ............. 702/28 |
| 5,868,496 | A | * | 2/1999 | Spitzberg ................ 374/128 |
| 6,065,866 | A | * | 5/2000 | Kraus et al. ............... 374/2 |
| 6,072,150 | A | * | 6/2000 | Sheffer ................ 219/121.83 |
| 6,127,679 | A | | 10/2000 | Ashley et al. |
| 6,610,984 | B2 | * | 8/2003 | Knauth et al. ............ 250/352 |
| 6,652,452 | B1 | * | 11/2003 | Seifert et al. ............. 600/140 |
| 6,742,925 | B2 | * | 6/2004 | Maccarone ............... 374/2 |
| 7,041,963 | B2 | * | 5/2006 | El Rifai et al. ........... 250/234 |
| 7,111,980 | B2 | * | 9/2006 | Pavlidis et al. ............ 374/45 |
| 7,122,788 | B1 | * | 10/2006 | Owen et al. ............. 250/252.1 |
| 2001/0044588 | A1 | * | 11/2001 | Mault .................... 600/549 |
| 2002/0143257 | A1 | * | 10/2002 | Newman et al. ........... 600/474 |
| 2007/0187605 | A1 | * | 8/2007 | Micko .................. 250/339.04 |

OTHER PUBLICATIONS

International Search Report for international application PCT/GB2004/001778 dated Nov. 19, 2004.

International Preliminary Report on Patentability for international application PCT/GB2004/001778 dated Apr. 1, 2005.

Ring, F. J., "Criteria for Thermal imaging in Medicine," pp. 1697-1698 from *Engineering in Medicine and Biology Society*, from IEEE Annual Conference held Sep. 20-23, 1995 in Montreal Quebec, Canada, 1995.

Written Opinion for international application PCT/GB2004/001778.

Hsieh et al., "Focal-Plane Arrays and CMOS readout techniques of infared imaging systems," *IEEE Trans. on Circuits and Systems for Video Technology*, 7(4):594-605 (Aug. 1997).

Jones, B. F., "A Reappraisal of the Use of Infared Thermal Image Analysis in Medicine," *IEEE Trans. on Medical Imaging*, 17(6):1019-1027 (Dec. 1998).

* cited by examiner

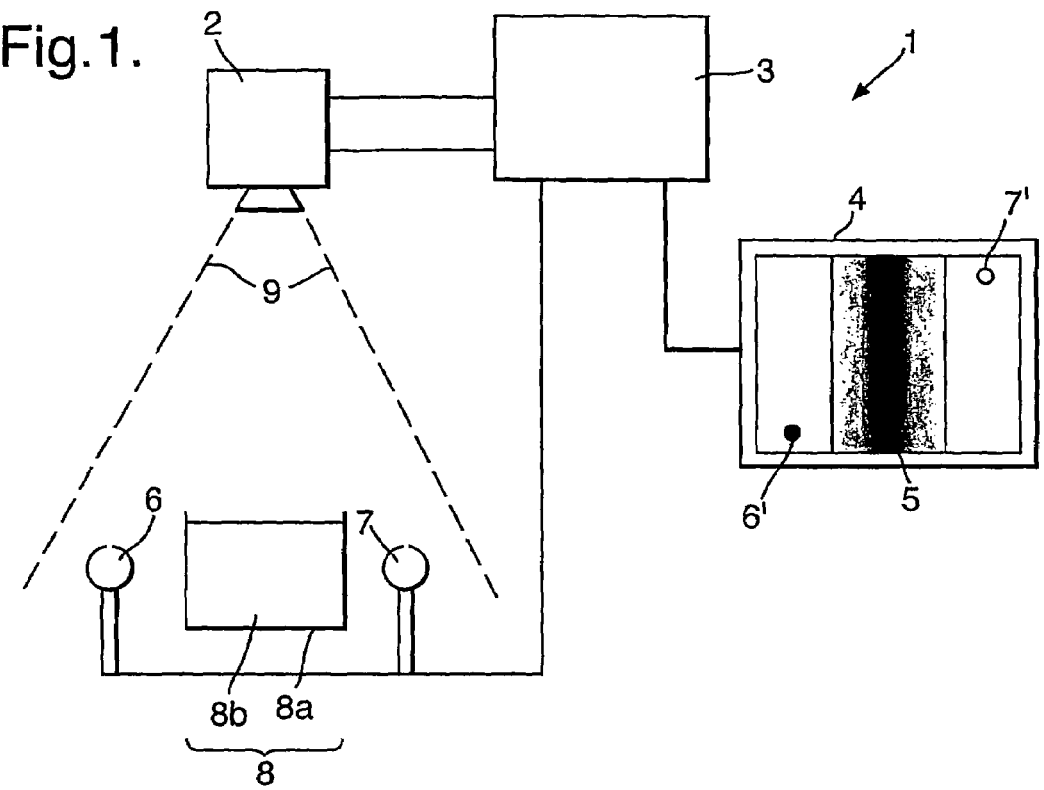
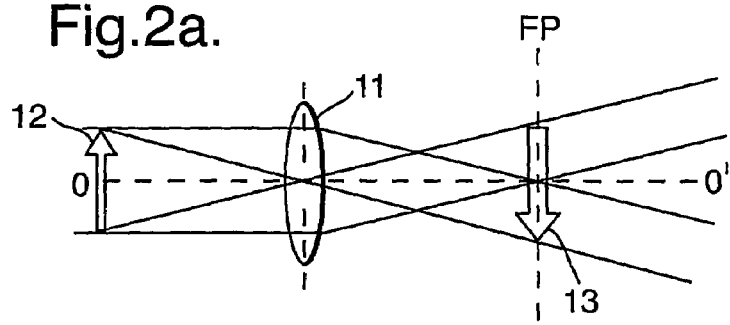
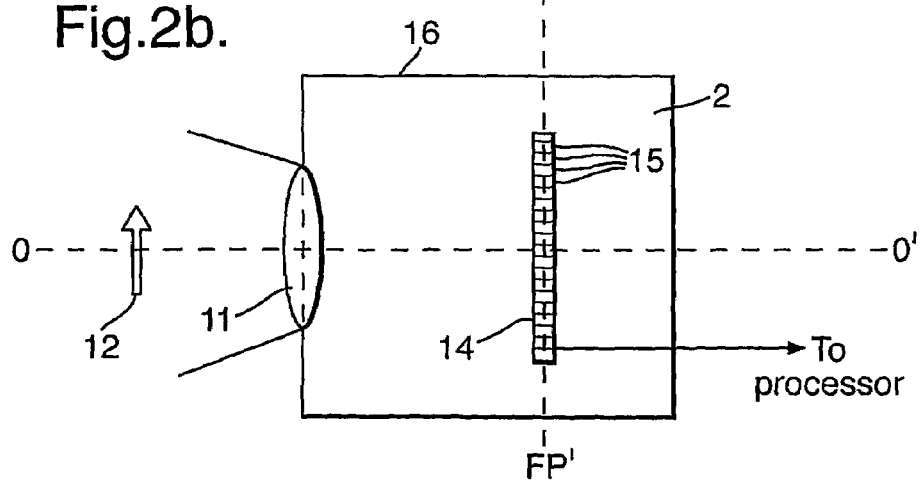

THERMAL IMAGING SYSTEM AND METHOD

This application is a National Stage of Application No. PCT/GB2004/001778, filed Apr. 23, 2004, which claims priority to British Application No. GB 0309479.4, filed Apr. 25, 2003 and British Application No. GB 0310334.8, filed May 6, 2003.

This invention relates to a thermal imaging system and method for generating high precision temperature images of a scene.

Thermal imagers provide two dimensional temperature images of a scene. Typically, such devices observe and measure infrared emission from the scene, thus providing a measure of temperature without being in contact with the source. Infrared energy is emitted by all materials at temperatures above absolute zero. This energy travels in the form of electromagnetic waves with wavelengths typically in the range 0.7 microns to 20 microns. When an infrared ray is intercepted by a body which is not transparent to the infrared spectrum, it induces electronic transitions or its energy is converted into heat and the infrared rays may be observed.

On striking a material surface, part of the infrared energy will be absorbed, some will be reflected and the remainder transmitted through the object. Of the energy absorbed by the material, a proportion may be re-emitted. Together, these phenomena determine the "emissivity" of the material. A "black body" is a hypothetical object or system which does not reflect or transmit any infrared energy incident upon it. All such radiation is absorbed and the black body re-radiates energy characteristic of the its temperature only. A true black body has an emissivity of 1 but the nearest that can be achieved in practice is about 0.998, using an infrared opaque cavity with a small aperture.

Infrared imaging systems convert the energy transmitted in the infrared spectrum into a visible light image. This is generally termed "thermography" and has applications in a wide range of fields ranging from monitoring metal melts to night vision or security imaging. Other applications include medical imaging, process control and non-destructive testing. Generally speaking, such applications fall into one of two categories. Surveillance applications such as criminal tracking or building inspection require high resolution images but low accuracy temperature measurements are acceptable. On the other hand, industrial and medical uses require radiometric images which provide quantitative readings of the temperatures observed.

Several types of infrared sensing devices are available. A spot or point radiometer measures radiation from one particular point at a time, and outputs a reading showing the temperature of that point. A thermal line scanner shows radiant temperature along a line. A thermal imaging camera produces a temperature map of the full scene. Typically, thermal imaging cameras make use of a focal plane array (FPA) detector to observe the infrared energy emitted from a scene. FPA detectors consist of an array of detectors positioned in the plane at which the image of the scene is focussed. This results in high resolution thermal images. Conventional radiometric FPAs use photon detectors which effectively count infrared photons over a short period of time. Typical detectors are fabricated from mercury cadmium telluride material in various compositions. In typical industrial use, these detectors have a long wavelength sensitivity cut-off at about 5 microns and must be cooled to temperatures of approximately −80° C. Such imaging devices based on photon detectors achieve high accuracy but are complex and expensive. Some industrial applications benefit from sensing at longer wavelengths, for example in the wavelength region 8 to 14 microns. Photon detector arrays can be made to operate at these wavelengths but require even more cooling, typically down to −200° C. and the resulting instruments are even more complex and expensive.

A new generation of imagers has recently emerged which use uncooled focal plane array detectors. An array of, typically, bolometers is located in the camera's focal plane. On striking the bolometer, an incident infrared ray will cause an increase in the temperature of the bolometer and therefore a change in its electrical resistance. The resistance of the bolometer may be measured and the incident infrared energy calculated. Detectors other than bolometers may be used, for example thermopiles or pyroelectrics. They are referred to as thermal detectors since the detection process involves the conversion of infrared energy to heat. The main advantage of a thermal detector array is that it may be operated at close to room temperature. The complex cooling systems of previous FPAs are therefore not required and the resulting thermal imaging device is simpler, smaller and less expensive. Thermal detectors are also wideband; that is they respond equally to infrared radiation of all wavelengths, in particular they do not exhibit the sharp long-wavelength cut-off typical of photon detectors.

Thermal imagers based on uncooled FPA detectors are very sensitive but not very radiometric: the relation between the image and the temperatures in the scene is only semi-quantitive. In part, this is due to the fact that uncooled FPA detectors are typically operated at long wavelengths, typically 8 to 14 microns and as a consequence are influenced by emissions from the internal parts of the camera. As such, imaging devices based on this technology are useful for surveillance but are not suitable for use in industrial applications which require more accurate knowledge of the measured temperatures. It would be advantageous to improve the accuracy of the image output from an uncooled FPA camera, resulting in a highly quantitative temperature imaging apparatus which is inexpensive and suitable for industrial use. One application in which such an apparatus would be particularly desirable is monitoring the temperature of metal heat exchangers during testing. Conventional techniques require thermometers to be in contact with the metal heat exchanger which, in practice, allows only a small number of point measurements. What is needed is an apparatus which produces a detailed, spatially-resolved, temperature map with high temperature accuracy.

WO03/077539, for example, proposes a method of calibrating an infrared camera by use of an advance calibration sequence. The method involves exposing the detector to a reference surface at a known temperature and for a known time. This is repeated several times in order to characterise the response of each pixel in the detector array. The results are stored and used to calibrate subsequent measurements made by the detector. The method is particularly adapted for the situation in which the reference surface is, by necessity, at a substantially different temperature to that of the object to be measured. The requirement of a pre-measurement calibration sequence however is undesirable as it results in a complex temperature measurement method and increases the amount of time needed to set up and obtain the measurement.

In accordance with the present invention, a thermal imaging system for quantitative thermal mapping of a scene comprises a thermal imaging device; a first heat source of known temperature and emissivity, located within the scene viewed by the thermal imaging device; and a processor adapted to generate a calibrated temperature map of the scene from the data supplied by the thermal imaging device, based on the known temperature of the heat source.

By providing the imaging system with a known temperature reference point, the data supplied by the thermal imaging device may be calibrated resulting in a highly radiometric output image. This makes it possible to use uncooled focal plane array detector technology to produce accurate temperature measurements suitable for industrial applications, whilst remaining inexpensive and straightforward to use.

By placing the heat source in the field of view of the thermal imaging device, for example alongside the object whose temperature is to be measured (which also remains in the field of view), calibration and temperature measurement may effectively be carried out simultaneously. This removes the need for an advance calibration sequence and so makes the thermal imaging system easy to use and versatile.

The invention further provides a method of generating a quantitative thermal map of a scene, the method comprising positioning a first heat source of known temperature and emissivity within the scene; imaging the scene using a thermal imaging device; and generating a calibrated temperature map of the scene, based on the known temperature of the heat source, using a processor.

Alternatively, "natural" objects in the scene may be used as heat sources, in which case the invention further provides a method of generating a quantitative thermal map of a scene, the method comprising:

selecting at least part of an object in the scene, of known emissivity;

measuring the temperature of the at least part of an object, the at least part of an object becoming a first heat source;

imaging the scene using a thermal imaging device; and generating a calibrated temperature map of the scene, based on the measured temperature of the heat source.

The invention may therefore be used in a number of different applications, including temperature monitoring of metal heat exchangers. A further important example is in the monitoring of the surface temperatures of living subjects such as humans or animals, with a view to identifying subjects which may be suffering from a disease.

Preferably, the thermal imaging system further comprises a second heat source of known temperature and emissivity, located within the scene viewed by the thermal imaging device and the processor is adapted to generate the calibrated temperature map from the data supplied by the thermal imaging device, based on the known temperatures of both the first and the second heat sources. By providing the system with two known temperature reference points, the processor is able to more accurately determine the correction required to calibrate the image.

Generally, the thermal imaging system further comprises means for measuring the temperature of the or each heat source and communicating the temperature to the processor. The temperature of the heat sources may be measured by various means such as a contact sensor or an infrared thermometer. The temperatures may be adjustable by electronic means such as resistance heating means or a device operating on the Peltier principle. Preferably, the control of each heat source is effected by electronic circuitry local to that heat source with the set-point temperature communicated from the processor. Typically, the temperatures of the heat sources will be controlled to just above and just below the temperatures of interest in the scene.

Preferably the or each heat source is located close to the target object of primary interest in the scene. This has the effect that atmospheric absorption in the sight path to the target, for example caused by smoke or fume, affects the measurement of the heat sources and the target object equally and is calibrated out by the system.

Preferably, a temperature range of the thermal imaging device is adjustable by the processor. Typically, this temperature range is adjustable by the processor in accordance with the known temperature of the or each heat source. This enables the system to be optimised and thereby produce the most accurate and highest resolution image of the scene as possible.

Generally, the thermal imaging device comprises a focal plane array (FPA) detector and preferably the FPA detector is an uncooled FPA detector. Preferably, the thermal detectors are bolometers and the thermal imaging system further comprises means for maintaining the temperature of the FPA detector at close to room temperature. Typically, the temperature of the FPA detector is maintained by means of a device operating on the Peltier principle.

Typically the imaging device is encased in a protective housing. This may include an internal heater, controlled by a thermostat, and provision for liquid cooling. The housing may also incorporate an air purging system and a protection window.

Preferably the or each heat source has a surface finish substantially identical to that of the target object of primary interest in the scene. In this case reflected radiation affects the measurement of the heat sources and the target object equally and is calibrated out by the system. For example, it is preferable that the or each heat source comprises at least a portion of an object forming part of the scene to be thermally mapped, in which case the temperature of the object may be measured using contact thermometers, for example.

In situations where it is not practicable to mimic the target object's surface finish, preferably, the or each heat source is a black body source. In practice, the sources will not be perfect black bodies but may be close approximations with a high and stable emissivity due to a cavity structure or an appropriate coating.

Some examples of thermal imaging systems in accordance with the present invention will now be described with reference to the accompanying drawings, in which:

FIG. 1 is a schematic diagram depicting a thermal imaging system imaging a scene;

FIG. 2a is an optical ray diagram indicating the position of the focal plane in a converging lens system;

FIG. 2b is a schematic representation of a thermal imaging device comprising a focal plane array detector;

Figure 3A:
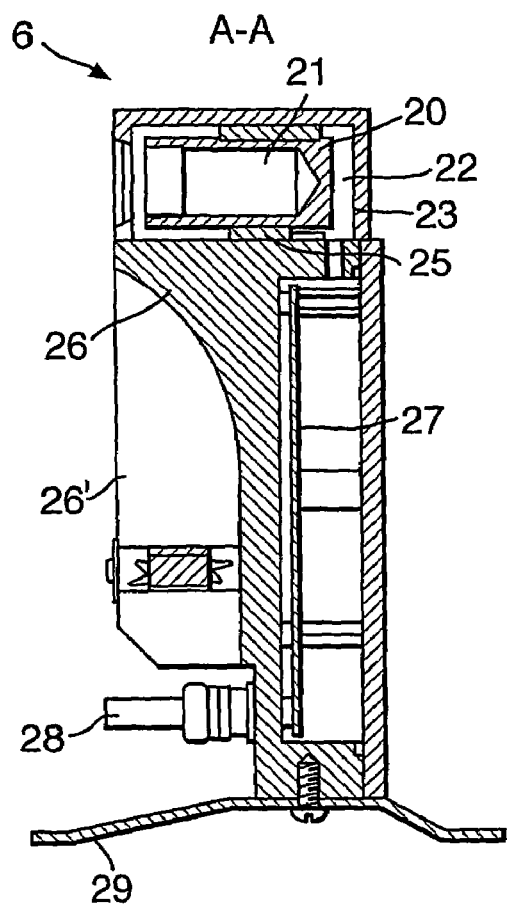
FIGS. 3a to 3c show an example of a reference heat source which may be used in the thermal imaging system of FIG. 1.

The thermal imaging system 1 depicted schematically in FIG. 1 comprises a thermal imaging device 2, connected to a processor 3 which in turn communicates with heat sources 6 and 7 and display device 4. The thermal imaging device 2 has a field of view (defined by dashed lines 9) which includes both heat sources 6 and 7 and an object 8. In this example, the object 8 comprises a conveyor belt 8a carrying hot material 8b, for example molten metal. The heat sources 6 and 7 are placed in the scene to be imaged, at the same time as the imaging, and are external to the thermal imaging device 2. It is helpful to place the heat sources 6 and 7 close to the object 8.

The heat sources 6 and 7 are designed to emulate black body sources, having a high and stable emissivity. The processor 3 communicates with the heat sources 6 and 7 to control the temperature of each heat source 6 and 7 and to know the accurate temperature of the heat source 6 and 7 at all times. The temperature of each heat source 6 or 7 may be measured by a variety of means including a contact sensor or an infrared thermometer. Each heat source may be set to the desired temperature by electronic means such as resistance heating means or a device operating on the Peltier principle, for example. The temperature of each heat source is set to be close to that of the scene to be imaged. The accuracy of the calibration is improved by maintaining the two heat sources 6,7 at just above and just below the temperature of the object 8 whose temperature is to be measured.

Thermal imaging device 2 receives the infrared energy emitted from all of the bodies within its field of view. The thermal imaging device 2 detects the incident infrared energy and converts it into electrical signals which are passed to the processor 3. The processor 3 uses this data to form a virtual thermal image of the scene, comprising an array of pixels. The image is "virtual" because it is not output from the processor 3. Each pixel corresponds to one of the detectors 15 in the thermal imaging device 2 and is indicative of the quantity of infrared energy incident on that detector 15. This is a measure of the temperature of a portion of the scene viewed by the thermal imaging device 2.

The heat sources 6 and 7 are imaged onto localised areas of the detector array and represented by two groups of pixels in the virtual image. It is usual that the group of pixels include only a subset of the pixels making up the whole virtual image. The remaining pixels represent the various objects 8 in the scene. The temperature indicated by each group of pixels is known to correspond to the known temperature of its respective heat source 6 or 7. The processor uses these pixels and the known temperatures and of the heat sources 6 and 7 to determine the offset between the actual temperature and the temperature indicated by the pixels. This correction is then applied to the entire virtual image, resulting in a calibrated temperature map 5 of the scene in which the temperatures of the various bodies are represented by different colours from the visible spectrum.

If the heat sources 6 and 7 have the same emissivity as the target objects of interest then the calibration calculation is as follows:

Let the uncorrected camera temperatures for the first heat source 6, the second heat source 7, and a target point be t1, t2 and t3 respectively, and the true, known temperatures of the heat sources 6 and 7 be T1 and T2 respectively. The true temperature of the target point T3 is then:

$$T3 = A \cdot t3 + B$$

where A and B are constants found by solving:

$$T1 = A \cdot t1 + B$$

$$T2 = A \cdot t2 + B$$

If the emissivities of the heat sources 6 and 7 and the target point are different but known to be E1, E2 and E3 respectively, then the calculation becomes:

$$E1 \cdot f(T1) = a \cdot f(t1) + b$$

$$E2 \cdot f(T2) = a \cdot f(t2) + b$$

where the functions f( ) are the Planck Radiation Function, multiplied by the spectral responsivity of the camera, integrated over the spectral bandwidth of the camera.

These two equations are solved for constants a and b, and then $$E3 \cdot (T3) = a \cdot f(t3) + b$$

is solved for f(T3)

T3, the true temperature of the target point, is then obtained by inverting the function f(T3). As shown, the calibration calculations are carried out based on the two known heat source temperatures and thus a series of measurements, e.g. at different exposure times, is not required. In fact, the exposure time need not be adjusted or specially controlled for operation of the calibration method.

It should be evident that the above treatment assumes similarity of behaviour between different pixels in the array. In practice, dissimilar behaviour may be pre-compensated for by various correction routines applied to the thermal imaging device, including non-uniformity and bad pixel corrections.

The calibrated temperature map 5 is output by the processor 3 to the visual display unit 4. In the example shown in FIG. 1, high temperatures are indicated by dark regions and cool temperatures by light regions. The heat sources 6 and 7, shown in the calibrated temperature map 5 as points 6' and 7', have different temperatures from one another. This need not be the case, but it is advantageous to arrange the heat sources in such a manner since the accuracy with which the image may be calibrated by the processor 3 is improved.

The calibrated temperature map 5 provides a quantitative measure of the temperature of each body within the field of view of the camera. The temperature of the object 8, or a portion of it, may therefore be accurately determined without the need for contacting thermometers or complex cooled FPA detectors. Further, there is no requirement for a calibration sequence to be carried out in advance.

The thermal imaging device 2 is shown in more detail in FIGS. 2a and 2b. FIG. 2a indicates the position of the focal plane (FP) in a converging lens system. Light or infrared rays are depicted as straight solid lines. It can be seen that an object 12 is inverted and magnified by the lens 11 to form an image 13 at a distance f behind the lens 11. This distance f is the focal distance of the lens 11, and the plane in which the image 13 is formed is the focal plane (FP).

In this example, the thermal imaging device 2 comprises a focal plane array (FPA). In FIG. 2b an array 14 of detectors 15 is shown to lie on the focal plane. Infrared rays (not shown) enter the thermal imaging device 2 through a lens 11 and form an image of the scene (in this case the object 12) on the array 14. Each detector 15 detects the amount of infrared energy incident upon it and converts the measured energy to an electrical signal which is communicated to the processor 3. As previously described, the processor 3 uses this data to generate a temperature map of the scene.

The detectors 15 are typically bolometers which may be operated at approximately ambient temperature. The bolometers may be fabricated from materials such as amorphous silicon or vanadium oxide using processes such as micro-machining or etching. Incident infrared energy causes the bolometer to heat up, thereby changing its electrical resistance. The resistance of each bolometer is measured using a biassing means (not shown). Alternative types of detectors 15 may be used in place of bolometers, for example thermopile or pyroelectric detectors.

The thermal imaging system 2 is cased in a protective housing 16. This may include an internal heater, controlled by a thermostat, and also provision for liquid cooling. The array 14 of detectors 15 may be maintained at its operational temperature by a device operating on the Peltier principle. The housing 16 may also incorporate an air purging system and a protection window. These optional features are not shown in the Figures.

Conventional FPA thermal imaging cameras have limited signal drive capability and the read out must be located within a few metres of the camera. In the arrangement shown, the camera is connected on a short cable to a user interface box. This provides long cable drive capability so that the processor can be mounted up to 1 kilometre from the camera. It also provides a convenient connection point at which to couple such a thermal imaging device with the processor 3. Also during system installation and commissioning, a local visual display unit may be connected at this point to view the received image, thereby assisting the setting-up of the apparatus.

The above described system is capable of very high precision temperature measurement, typically within fairly localised areas of the scene viewed by the imaging device, and within reasonably narrow temperature limits. For example, the target object 8 may fill perhaps 20% of the scene and its temperature might be known to within 25-35° C. The heat sources 6 and 7 may then be set to 25° C. and 35° C. respectively and the temperature of the object 8 could be determined (by the imaging system) to approximately 0.5° C. The thermal imaging system allows this to be achieved with a low cost, general purpose thermal array imaging device whose pre-calibration may be over a wide span (e.g. 0-300° C.) and whose accuracy, without the reference source correction, may be quite poor (e.g. ±4° C.).

A second example of the use of a system according to the invention is now described. In this case the system is adapted to be sensitive to body heat radiated from human subjects. The purpose of this second example is to detect abnormalities in the temperatures of human subjects. One example of this is in providing screening for circulatory problems in the limbs of human subjects. Poor circulation often manifests itself in low temperatures of peripheral body parts such as hands.

An further important example is in the detection of elevated body temperatures in human subjects, this being indicative of disease. In this example, the modified apparatus described above is installed at a point of entry into a country (such as an airport). The temperatures of the faces of travellers passing into the country are then monitored with the system. It is convenient to use the faces of subjects since these are frequently not covered and exhibit sufficient variations in temperature for disease detection and screening. Travellers suffering from certain infectious diseases are often found to exhibit elevated temperatures above the 37 Celsius norm. The maximum temperatures are found on the faces of subjects where the eyes meet the nose. Temperatures are elevated in diseased subjects by up to 4 Celsius in such regions. These can be detected reliably with the system described.

The apparatus described above is therefore modified to detect such temperature variations in human subjects. The imaging device 2 is installed above a doorway or passenger thoroughfare. Images of the human subjects (each subject acting as the object 8 in FIG. 1) are then obtained. The heat sources 6 and 7 are also heated to specific temperatures (typically around 37 Celsius) to achieve this. These are again placed within the view of the imaging device 2.

When a human subject exhibiting an elevated temperature is detected, a signal is produced and the system operator is alerted. The subject so identified can then be subjected to further questioning and/or medical tests to ascertain the reason for their high temperature.

The system according to this example is therefore extremely valuable in controlling the spread of diseases such as influenza and the SARS (Severe Acute Respiratory Syndrome) virus.

Figure 3B:
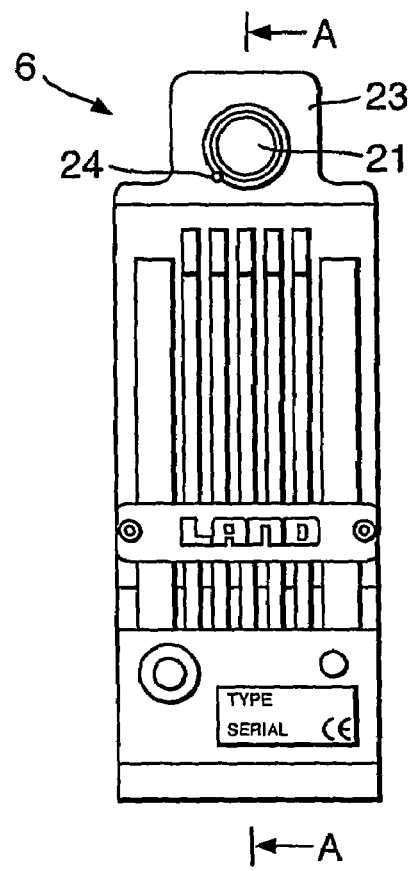

FIG. 3 shows a preferred embodiment of a reference heat source which could be used in the above described thermal imaging system, for instance as heat source 6. FIG. 3A shows a cross-section through the heat source 6 along the line A-A shown in FIG. 3B.

The heat source 6 includes a miniature reference source in the form of a black body cavity 21 mounted on a heat sink 26 and provided with convenient control and connection means 27,28. The heat source 6 has a stand 29 for easy positioning of the heat source 6 close to the object 8 in the field of view of the thermal imaging device 2 (see FIG. 1).

Figure 3C:
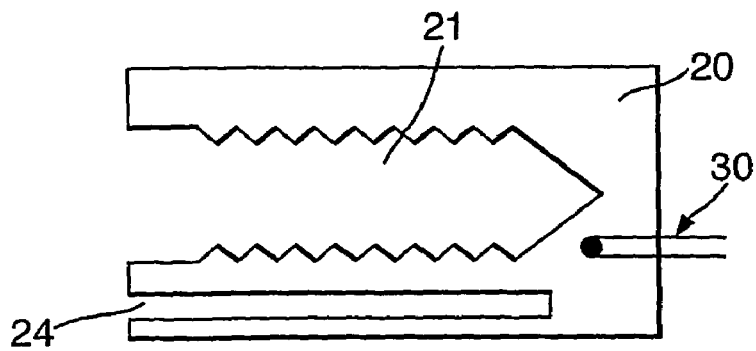

The reference source itself is shown enlarged in FIG. 3C. This consists of a black body cavity 21 defined by cavity wall 20 which is typically made of metal. The inside of the cavity is generally grooved as shown in FIG. 3C and painted matt black in order to make the apparatus closely approximate to a true black body. Cavity wall 20 is surrounded by an airspace 22 inside an insulating housing 23. A temperature control sensor is embedded in cavity wall 20 and connected to circuit board 27. The control sensor 30 may typically be a thermistor. This is used to monitor the temperature of the black body cavity 21. However, the cavity wall 20 may optionally also be provided with a bore 24 into which a second reference temperature sensor may be inserted. This sensor could be selected and inserted by the system user and, for example, it may be a resistance thermometer calibrated by a national laboratory. Bore 24 is open at the front of the heat source 6 for easy user access.

A Peltier device 25 is provided adjacent to cavity wall 20 and controlled by the circuit board 27 so as to heat or cool the black body cavity 21 as required to maintain the reference source at the desired temperature.

The heat source 6 depicted in FIG. 3 is a convenient and usable example of a suitable reference source, but many other types of heat source could be used without departing from the scope of the invention.

Figure 4:
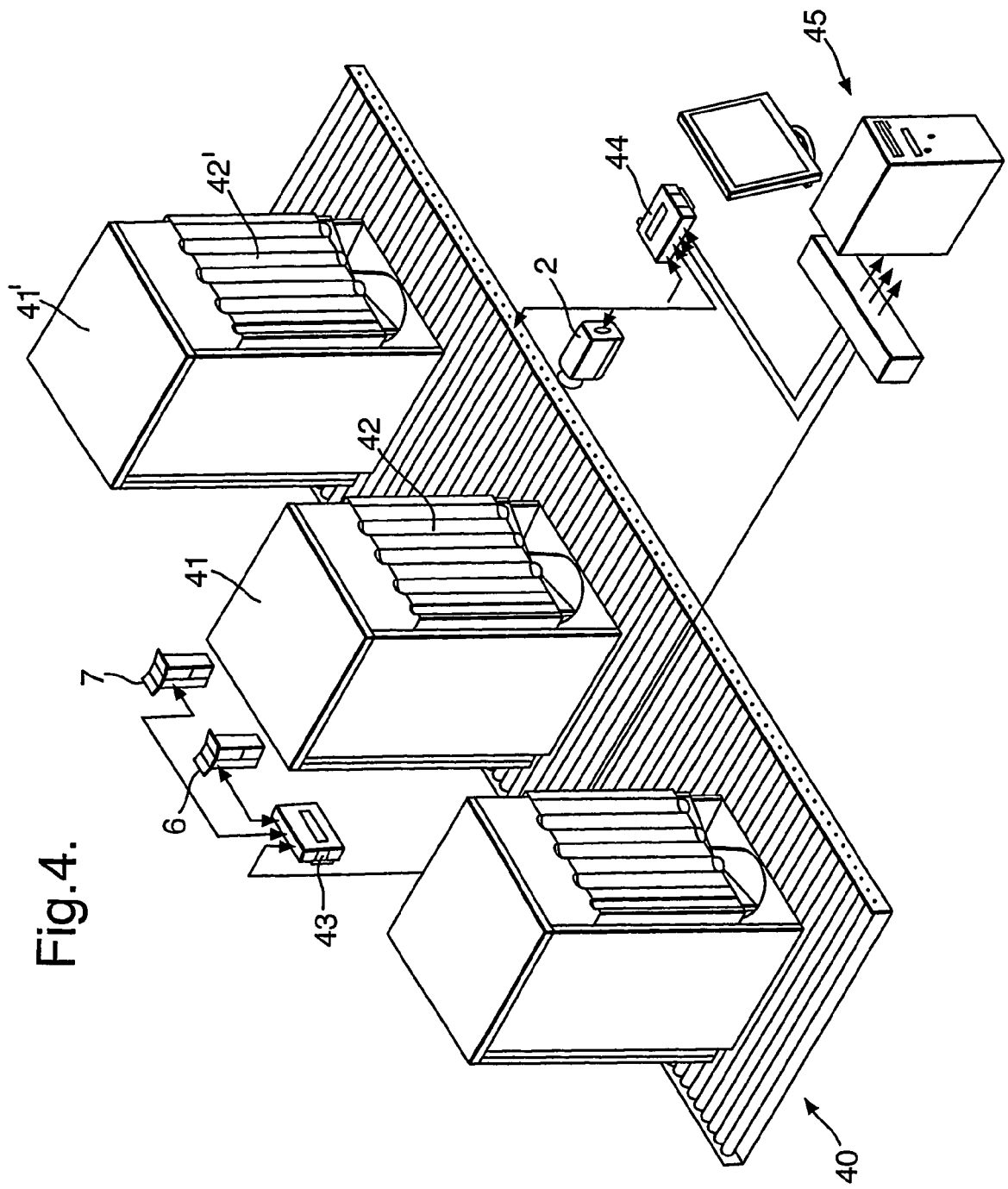
FIG. 4 shows the thermal imaging system in use in an example application.

FIG. 4 shows a further example of the use of a system according to the invention. In this application, the thermal imaging system is used to check refrigerator heat exchangers. On a production line 40, the fridges 41, 41' etc are moved along a conveyor and stopped at a reference position in front of a thermal imaging device 2. Also in the field of view of the imaging device 2 are reference heat sources 6 and 7 situated close to the reference position. As described above, the temperature of each heat source 6, 7 is chosen so as to be close to the expected temperature of the heat exchanger 42. An image of the refrigerator heat exchanger 42 is taken by the thermal imaging device 2 and corrected to high temperature precision using the above described method based on the two reference sources 6 and 7 placed in the field. Connection boxes 43 and 44 convey the data to a computer 45 where the corrected image may be compared against a reference image of what an ideal heat exchanger should look like. Defects and anomalies in the heat exchanger 42 may therefore be identified and repaired if necessary.

A still further example of the use of a system according to the invention is application of the system to the situation in which "natural" objects in the scene are instrumented with precision contact thermometers and are used themselves as reference sources. Essentially, one or more objects already present in the scene to be imaged are selected and their temperatures precisely measured and monitored. These known temperature points act as reference sources and allow the thermal imaging system to generate calibrated temperature maps as previously described.

This mode could be used for example in surgery, in particular laser surgery. Skin areas of the patient adjacent to the "wound" or target area, are fitted with contact thermometers. These areas have the same emissivity as the target area. Thus, using the above described method, an image taken by a thermal imaging device directed onto the target area and its surroundings may be corrected for both camera defects and for emissivity uncertainties Of course, this method of using "natural" objects as reference heat sources is not limited to use in surgery and could be applied to many other situations including the monitoring of metal melt temperatures or even the imaging of refrigerator heat exchangers as shown in FIG. 4. For example, accurate thermometers could be affixed to one or more points on the heat exchanger 42 and used in place of, or in addition to, reference sources 6 and 7.

The invention claimed is:

1. A thermal imaging system for quantitative thermal mapping of a scene containing at least one target object, the system comprising:
   a thermal imaging device for detection of radiation emitted by the scene, the thermal imaging device comprising a focal plane array (FPA) detector having a plurality of detectors arranged in an array that includes a first subset of detectors having fewer than all of the detectors in the FPA and a remainder of other detectors;
   a first heat source of known temperature and emissivity, located within the scene viewed by the thermal imaging device; and
   a processor adapted to generate a calibrated temperature map of the scene from the data supplied by the thermal imaging device, by determining a correction based on the known temperature of the first heat source and detected radiation data from the first subset of detectors which first subset receives radiation from the first heat source while the remainder of other detectors in the FPA receives radiation from other portions of the scene at the same time, and applying the correction to detected radiation data supplied by the FPA to thereby generate the calibrated temperature map.

2. A thermal imaging system according to claim 1 which further comprises a second heat source of known temperature and emissivity, located within the scene viewed by the thermal imaging device and wherein the processor is adapted to generate the calibrated temperature map from the data supplied by the thermal imaging device, based on the known temperatures of both the first and the second heat sources.

3. A thermal imaging system according to claim 1 which further comprises means for measuring the temperature of the heat source and communicating the temperature to the processor.

4. A thermal imaging system according to claim 3 wherein the temperature of the heat source is measured by a contact sensor.

5. A thermal imaging system according to claim 3 wherein the temperature of the heat source is measured by an infrared thermometer.

6. A thermal imaging system according to claim 1 wherein the temperature of the heat source is adjustable by electronic means.

7. A thermal imaging system according to claim 6 wherein the temperature of the heat source is adjustable by resistance heating means.

8. A thermal imaging system according to claim 6 wherein the temperature of the heat source is adjustable by a device operating on the Peltier principle.

9. A thermal imaging system according to claim 1 wherein the control of the heat source is effected by electronic circuitry local to that heat source.

10. A thermal imaging system according to claim 9 wherein a set-point temperature for control of the heat source is communicated from the processor to the electronic circuitry local to that heat source.

11. A thermal imaging system according to claim 1 wherein a temperature range of the thermal imaging device is adjustable by the processor.

12. A thermal imaging system according to claim 11 wherein the temperature range is adjustable by the processor in accordance with the known temperature of the heat source.

13. A thermal imaging system according to claim 1 wherein the FPA detector is an un-cooled FPA detector.

14. A thermal imaging system according to claim 1 wherein the FPA comprises thermal detectors.

15. A thermal imaging system according to claim 14 wherein the thermal detectors are bolometers.

16. A thermal imaging system according to claim 1 which further comprises means for maintaining the temperature of the FPA detector at close to room temperature.

17. A thermal imaging system according to claim 16 wherein the temperature of the FPA detector is maintained by means of a device operating on the Peltier principle.

18. A thermal imaging system according to claim 1 wherein the FPA detector is cased in a protective housing.

19. A thermal imaging system according to claim 1 wherein the heat source has a surface finish substantially identical to that of an object of primary interest in the scene.

20. A thermal imaging system according to claim 1 wherein the heat source comprises at least a portion of an object forming part of the scene to be thermally mapped.

21. A thermal imaging system according to claim 20 wherein the temperature of the object is monitored using at least a contact thermometer fitted to the object.

22. A thermal imaging system according to claim 1 wherein the heat source is a black body source.

23. A thermal imaging system according to claim 1 wherein the system is adapted to identify temperature variations in at least part of a target object within the scene, the target object being a living subject.

24. A thermal imaging system according to claim 23, wherein the living subject is a human.

25. A thermal imaging system according to claim 24, wherein the part of the target object is a hand, foot or face.

26. A thermal imaging system according to claim 1, wherein the first heat source and the at least one taget object are located alongside each other within the scene, such that any atmospheric absorption occurring between the first heat source and the thermal inaging device is substantially the same as any occurring between the at least one taget object and the thermal inaging device.

27. A thermal imaging system according to claim 1 wherein the scene corresponds to the field of view of the thermal imaging device.

28. A thermal imaging system according to claim 1 wherein the correction is applied to detected radiation data from each of the detectors in the FPA which receives radiation from the scene.

29. A thermal imaging system according to claim 2 wherein the correction is further based on the known temperature of the second heat source and detected radiation data from a second subset of the detectors in the FPA, which second subset receives radiation from the second heat source.

30. A thermal imaging system according to claim 1 wherein the temperature of the first heat source is known independently of the thermal imaging device.

31. A thermal imaging system according to claim 2 wherein the temperature of the second heat source is known independently of the thermal imaging device.

32. A methid of generating a quantitative thermal map of a scene containing at least one target object, the method comprising:
- positioning a first heat source of known temperature and emissivity within the scene;
- detecting radiation emitted by the scene using a thermal imaging device for detection of radiation emitted by the scene, the thermal imaging device comprising a focal plane array (FPA) detector having a plurality of detectors arranged in an array that includes a first subset of detectors having fewer than all of the detectors in the FPA and a remainder of other detectors; and
- generating a calibrated temperature map of the scene, by determining a correction based on the known temperature of the first heat source and detected radiation data from the first subset of detectors, which first subset receives radiation from the first heat source while the remainder of other detectors in the FPA receives radiation from other portions of the scene at the same time, and applying the correction to data supplied by the thermal imaging device.

33. A method according to claim 32 further comprising positioning a second heat source of known temperature and emissivity within the scene and generating the calibrated temperature map of the scene based on the known temperatures of both heat sources.

34. A method according to claim 32 which further comprises monitoring the temperature of the heat source and communicating the temperature (s) to a processor.

35. A method according to claim 32 further comprising identifying temperature variations in at least part of a target object within the scene, the target object being a living subject.

36. A method according to claim 35, wherein the living subject is a human.

37. A method according to claim 36, wherein the part of the target object is a hand, foot or face.

38. A method according to claim 35 wherein the method further comprises issuing a signal if the measured temperature of the subject is in excess of a threshold.

39. A method according to claim 38, wherein the method is repeated for a number of different living subjects so as to distinguish those with an elevated body temperature with respect to those exhibiting a normal body temperature.

40. A method according to claim 32 which further comprises communicating a set-point temperature to the heat source, and thereby controlling the temperature of the heat source.

41. A method according to claim 32 which further comprises controlling a temperature range, of the thermal imaging device, in accordance with the temperature of the heat source.

42. A method according to claim 32 wherein the first heat source and the at least one target object are located alongside each other within the scene, such that any atmospheric absorption occurring between the first heat source and the thermal imaging device is substantially the same as any occurring between the at least one target object and the thermal imaging device.

43. A method according to claim 32 wherein the scene corresponds to the field of view of the thermal imaging device.

44. A method according to claim 32 wherein the correction is applied to detected radiation data from each of the detectors in the FPA which receives radiation from the scene.

45. A method according to claim 33 wherein the correction is further based on the known temperature of the second heat source and detected radiation data from a second subset of the detectors in the FPA, which second subset receives radiation from the second heat source.

46. A method according to claim 32 wherein the temperature of the first heat source is known independently of the thermal imaging device.

47. A method according to claim 33 wherein the temperature of the second heat source is known independently of the thermal imaging device.

48. A method of generating a quantitative thermal map of a scene, the method comprising:
- selecting at least part of an object in the scene, of known emissivity;
- measuring the temperature of the at least part of an object, the at least part of an object acting as a first heat source;
- imaging the scene using a thermal imaging device for detection of radiation emitted by the scene, the thermal imaging device comprising a focal plane array (FPA) detector having a plurality of detectors arranged in an array that includes a first subset of detectors having fewer than all of the detectors in the FPA and a remainder of other detectors; and
- generating a calibrated temperature map of the scene, by determining a correction based on the known temperature of the first heat source and detected radiation data from the first subset of detectors, which first subset receives radiation from the first heat source while the remainder of other detectors in the FPA receives radiation from other portions of the scene at the same time, and applying the correction to detected radiation data supplied by the FPA.

49. A method according to claim 48 further comprising selecting a second at least part of an object in the scene of known emissivity, measuring its temperature such that it acts as a second heat source, and determining the correction based further on the known temperature of the second heat source and detected radiation data from a second subset of the detectors in the FPA, which second subset receives radiation from the second heat source.

50. A method according claim 48 which further comprises monitoring the temperature of the heat source and communicating the temperature (s) to a processor.

51. A method according to claim 48 further comprising identifying temperature variations in at least part of a target object within the scene, the target object being a living subject.

52. A method according to claim 51, wherein the living subject is a human.

53. A method according to claim 52, wherein the part of the target object is a hand, foot or face.

54. A method according to claim 51 wherein the method further comprises issuing a signal if the measured temperature of the subject is in excess of a threshold.

55. A method according to claim 54, wherein the method is repeated for a number of different living subjects so as to distinguish those with an elevated body temperature with respect to those exhibiting a normal body temperature.

56. A method according to claim 48 which further comprises communicating a set-point temperature to the heat source, and thereby controlling the temperature of the heat source.

57. A method according to claim 48 which further comprises controlling a temperature range, of the thermal imaging device, in accordance with the temperature of the heat source.

58. A method according to claim 48 wherein the temperature of the first heat source is known independently of the thermal imaging device.

59. A method according to claim 49 wherein the temperature of the second heat source is known independently of the thermal imaging device.

* * * * *